United States Patent
Mentink et al.

(10) Patent No.: US 6,811,604 B2
(45) Date of Patent: Nov. 2, 2004

(54) ADDITIVES FOR MINERAL BINDERS, BASED ON A PRODUCT OF INTERNAL DEHYDRATION OF A HYDROGENATED SUGAR, MINERAL BINDERS WITH ADDITIVES AND METHOD OF PREPARING SAME

(75) Inventors: Léon Mentink, Lille (FR); Jean-Pierre Graux, Lillers (FR)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 10/202,307

(22) Filed: Jul. 26, 2002

(65) Prior Publication Data

US 2003/0106465 A1 Jun. 12, 2003

Related U.S. Application Data

(62) Division of application No. 09/544,945, filed on Apr. 7, 2000, now abandoned.

(30) Foreign Application Priority Data

Apr. 8, 1999 (FR) ............................................ 99 04393

(51) Int. Cl.[7] .............................................. C04B 24/38
(52) U.S. Cl. ...................... 106/729; 106/730; 106/804; 106/819; 568/861; 568/863
(58) Field of Search ................. 106/729, 730, 106/804, 819; 568/861, 863

(56) References Cited

U.S. PATENT DOCUMENTS

| | | | |
|---|---|---|---|
| 3,484,459 A | * | 12/1969 | Hartmann |
| 4,073,658 A | | 2/1978 | Ohtani et al. |
| 5,626,666 A | | 5/1997 | Briat et al. |
| 5,880,182 A | * | 3/1999 | Minomiya et al. ............. 524/5 |

FOREIGN PATENT DOCUMENTS

| | | |
|---|---|---|
| EP | 0 650 941 | 5/1995 |
| GB | 1 085 594 | 10/1967 |
| GB | 1 508 761 | 4/1978 |
| GB | 2 293 821 | 4/1996 |
| JP | 45041393 | * 12/1970 |
| JP | 59121143 | * 7/1984 |

OTHER PUBLICATIONS

"Stereochemistry of Acid Catalysed Dehydration of hexitol" Cekovic J. Serb Chem. Society (19867,J1C4), p 205–11, 1986.*

Database WPI, XP002126264, 1984.
Database WPI, XP002126265, 1984.
Database WPI, XP002126266, 1974.

* cited by examiner

Primary Examiner—Paul Marcantoni
(74) Attorney, Agent, or Firm—Sturm & Fix LLP

(57) ABSTRACT

The subject matter of the invention is a new additive for mineral binders comprising a composition containing at least one product of internal dehydration of a hydrogenated sugar which can especially be a dehydrated hexitol such as isosorbide, isomannide, sorbitan or mannitan and which can be introduced at a rate of between roughly 0.001 and 5% (dry/dry) within any mineral binder, said additive being advantageously used as an accelerator for setting and/or hardening and/or as an agent for improving the mechanical properties of the mineral binder. It has a remarkable efficiency, including at low temperatures.

18 Claims, No Drawings

ADDITIVES FOR MINERAL BINDERS, BASED ON A PRODUCT OF INTERNAL DEHYDRATION OF A HYDROGENATED SUGAR, MINERAL BINDERS WITH ADDITIVES AND METHOD OF PREPARING SAME

CROSS-REFERENCE TO RELATED APPLICATIONS

This application is a Divisional of U.S. patent application Ser. No. 09/544,945, filed Apr. 7, 2000, now abandoned the disclosure of which is being incorporated herein by reference in its entirety.

The subject matter of the present invention is additives for mineral binders, based on a composition containing at least one product of internal dehydration of a hydrogenated sugar. The subject matter is also mineral binders with additives and the use of said additives or said compositions for the preparation of mineral binders.

By "mineral binder" is meant, in the sense of the present invention, any hydraulic binder, especially any mineral powder, capable of forming with water a paste, setting and hardening progressively even when sheltered from air. Usually, at ambient temperature, a mineral binder begins to form with water such a paste in a time span of roughly several minutes to less than 48 hours, generally between roughly 30 minutes and 24 hours. This definition is applied, amongst other things, to cements, to natural or artificial hydraulic limes, but also to mixtures, pasty or hardened, such as mortars, grouts, coatings and concretes, based on crushed cement and/or limes, water and/or aggregates (sands, gravels, pebbles . . . ), and finally to the raw materials going into the manufacture of cements such as pozzolanic cement, clinker cement, slag cement, calcareous fillers and silica fumes. By "mineral binder" is meant also any non-hydraulic binder based on calcium sulphate, gypsum and/or lime.

Depending on their final usages and conditions of use, it is sometimes necessary to add to mineral binders additives such as grinding agents or crushing aids, accelerators for setting and/or hardening, retarders of setting, plasticisers, water-reducing agents/plasticisers, superplasticisers and thickeners. These additives make it possible, for example, to modify the fluidity, pumpability, handling, setting, hardening, strength, durability and/or certain other properties of the mineral binder.

Numerous sugars and derivatives are already used in the preparation of additives for mineral binders, including:

molasses, which are inexpensive products, used as plasticisers;

sugars, which are very good plasticising water-reducing agents but strongly delay setting;

oxidised sugars, very good plasticising water-reducing agents, retarding agents for setting and which also make it possible to improve strength at 28 days as described in the patents FR 2 387 194 and GB 1 508 761;

hydrogenated sugars, which are plasticisers/water-reducing agents as described in the patent FR 2 726.550, but which are lesser retarding agents than the oxidised sugars whilst improving strength at 28 days, as results from the American patent U.S. Pat. No. 4,073,658;

hydrogenated or oxidised sugar syrups which are also described as grinding agents, according to patent EP 0 696 557;

esters of higher fatty acids and of polyols such as sorbitan trioleate which are agents for controlling the capacity for absorbing water and agents for improving the resistance to water and the adherence of cement compositions in the hardened state as described in the Japanese patent JP 59121143. These esters of higher fatty acids appear, moreover, to be retarders of setting and/or hardening.

Currently, for the preparation of cements, the tendency is to use products which are less expensive than clinker and/or to reduce the use of the latter. However, clinker provides good strength at 28 days. There exists therefore a need for an additive making it possible to correct the strength at 28 days of cements which do not contain clinker or contain little clinker.

Moreover, as regards mortars, grouts and concretes, the industry is searching for new accelerators of setting and/or hardening.

The setting and/or hardening accelerators conventionally used up till present are, on the one hand chlorinated products such as for example calcium chloride, and on the other hand non-chlorinated products, strongly acid or basic, such as for example respectively formic or sulphuric acids, their salts, lime, soda or products deriving therefrom (sodium metasilicates or aluminates).

Such accelerators are currently used particularly during the preparation of mineral binders intended to be used at low temperatures, i.e. at temperatures lower than roughly 15° C., or during the realisation in the factory of prefabricated articles.

However, the chlorinated products have the major drawbacks of being corrosive vis-à-vis enclosures for preparing the binders and the metal reinforcements utilised within the concretes used in civil engineering or the construction of buildings and of being a source of chlorine, a product known to be harmful to the environment.

For their part, the strongly acid or basic products present the drawbacks of being corrosive vis-à-vis metals and aggressive vis-à-vis the skin and the eyes and of not always making it possible to obtain sufficiently improved strengths when fresh and/or at 28 days.

Neutral and non-chlorinated products are sometimes used as accelerators of setting and/or hardening, such as lithium carbonate for example. However this compound has the drawback of being expensive in relation to the above-mentioned products.

Moreover, it has the tendency to reduce significantly the plasticity of the mineral binders and to be weakly effective at low temperatures.

There exists therefore a need to be able to have available an additive for mineral binders which, simultaneously:

is ecological, inoffensive during its use and non-corrosive vis-à-vis metals, is an accelerator of setting and/or hardening and makes it possible consequently to obtain improved strengths when fresh, sufficient to make possible rapid dismantling of formwork and this as much at ordinary temperatures as at low temperatures, confers a correct plasticity, if possible improved, to the mineral binders when they are used, and then confers to these binders mechanical properties at 28 days which are correct and if possible improved.

Within the framework of the present invention, what is meant by plasticity of the mineral binder is the capacity to obtain a Theological state in which the mineral binder can be handled, poured or pumped. The plasticity is measured according to the standardised method CEN 196-01, by which one measures in mm the spread of a given volume of mineral binder on a shock table.

The start and end of setting are measured with the aid of an automatic "prisomètre" with the trademark "ACMEL".

The mechanical strength when fresh is measured on specimens of mineral binder according to the standard CEN 196-01, quoted above, and this 17 or 24 hours after the manufacture of the specimens. This mechanical strength when fresh should, in general be greater than 5 Mpa to permit dismantling of the formwork. Moreover, the strength over time of the mineral binders (for example at 3 or 28 days) is also measured according to the above-quoted standard CEN 196-01.

The applicant company has had the merit of finding, after extensive research, that an additive meeting the above-quoted requirements of current technology could consist in a particular composition containing a selected sugar derivative.

In a more precise manner, the subject matter of the present invention is a new additive for mineral binders characterised in that it comprises a composition containing at least one product of internal dehydration of a hydrogenated sugar. In a surprising and unexpected manner, such dehydration products behave in a totally different manner from the hydrogenated sugars from which they are derived and which are known as being retarding agents as recalled above.

By "product of internal dehydration" is meant any product resulting, in any manner whatsoever, in one or several stages, from the removal of one or more molecules of water at the level of the original internal structure of a hydrogenated sugar and any compound containing, as a result especially of possible (poly)condensation phenomena, such a product. What is also meant is any compound resulting from the chemical modification and for example from the etherification of such a product or its esterification by a non-fatty chain. Such compounds can consist especially of acetylated, ethylated, methylated, propylated, butylated, ethylenated, propylenated derivatives of isosorbide or isomannide. It can also be in particular dimethyl isosorbide.

Preferably the hydrogenated sugar is a hydrogenated monosaccharide, especially chosen from hexitols, pentitols, tetritols, and their mixtures. It can also be a hydrogenated di-, oligo- or polysaccharide or any mixture of these products.

According to a particularly advantageous variant, the dehydration product stems from the internal dehydration, more or less forced, of a hexitol such as sorbitol, mannitol or galactitol for example and consists especially in a dehydrated hexitol chosen from isosorbide, isomannide, sorbitan, mannitan and any mixtures of at least any two of these products.

According to another variant, the composition contained in the additive according to the invention has a content of dehydration product(s) of at least 5%, preferably at least 10%, and more preferably at least 40%, these percentages being expressed in total dry weight of dehydration product(s) in relation to the dry weight of said composition.

The Applicant Company has found, as will be exemplified below, that compositions which have a total content of isosorbide and sorbitan of at least 15%, preferably of at least 55%, and more preferably still of at least 70%, were of particular interest as agents accelerating setting and/or hardening of mineral binders or as agents improving the mechanical properties of these binders.

And it is worth emphasising that such unexpected properties can be obtained:

for introduction rates in these compositions within the mineral binders, generally lower than the standard setting and/or hardening accelerators quoted previously, and just as well at ordinary temperatures, i.e. equal to or greater than roughly 15° C., as at low temperatures.

The subject matter of the present invention is also a mineral binder characterised in that it contains between roughly 0.001 and 5%, preferably between 0.01 and 2%, of an additive such as described above, these percentages being expressed in dry weight of the said additive in relation to the total dry weight of raw material(s) for cement, of cement and/or of lime contained in said mineral binder.

Contents of additive of the order of 0.1 to 1% can generally suit all mineral binders and all conditions, including of temperature, of their being placed and their hardening.

The additive according to the invention can be, or not be, constituted entirely of the composition based on the product(s) of dehydration described above.

In this case, the said composition can present itself in liquid, pasty or solid form.

The non-solid forms can have a very large range of dry matter (MS) for example an MS of between roughly 30 and 85%.

The proportion of dehydration product(s) such as described below in relation to the total dry matter of this composition, can also vary greatly as already explained.

These amounts and proportions of dry matter depend especially on the method of obtaining said composition. By way of non-restrictive example, this composition can consist:

in a reaction medium which is not purified, designated below "PRODUCT A", stemming from the standard dehydration of sorbitol under the effect of an acid and of the temperature, this medium having a dry matter of roughly 50% and a total content of isosorbide+sorbitan of roughly 75% (dry/dry), in a crystallised isosorbide powder of very high purity (purity=99%), designated below "PRODUCT B", coming from the direct distillation of PRODUCT A, in the residue of distillation obtained jointly with PRODUCT B, hereinafter designated "PRODUCT C", having a dry matter of roughly 58% and a total content of isosorbide+sorbitan of roughly 19% (dry/dry), in a PRODUCT A enriched with isosorbide and sorbitan, hereinafter designated "PRODUCT D", having a dry matter of roughly 79% and a total content of isosorbide+sorbitan of roughly 89% (dry/dry), in an enriched medium stemming from a double distillation of PRODUCT D, hereinafter designated "PRODUCT E", having a dry matter of roughly 83% and a total content of isosorbide+sorbitan of roughly 99%, in the residue of said double distillation such as obtained jointly with PRODUCT E, hereinafter designated "PRODUCT F", this residue having a dry matter of roughly 42% and a total content of isosorbide+sorbitan of roughly 89%, in pulverulent sorbitan of a purity of roughly 95%, hereinafter designated "PRODUCT G", and in pulverulent isomannide, of a purity of roughly 95%, hereinafter designated "PRODUCT H".

Such compositions, usable according to the invention, can have a pH within a wide range and in particular between roughly 2.5 and 6.5.

The additive according to the invention can also contain, apart from said composition, one or more additives traditionally used for the preparation of mineral binders, including at least one standard setting and/or hardening accelerator such as those quoted above.

The Applicant noted especially that it could be advantageous to associate a product of internal dehydration of a hydrogenated sugar such as isosorbide with lime or with sodium sulphate.

The additive thus obtained can also present itself in liquid, pasty or solid form.

Generally speaking, the additive according to the invention, constituted or not of the sole composition based on product(s) of internal dehydration of hydrogenated sugar(s), is completely appropriate for being used as an additive for cement and this before, during and/or after crushing, or as an additive for hydraulic limes. It is also completely appropriate for being used as an additive for concretes, grouts and mortars, whether they are liquid or solid.

The additive according to the invention can be introduced into the mineral binders according to a multitude of different ways. It can be introduced entirely during a particular stage of manufacture, storage, adding the additive, transport or placing of the mineral binder or in a divided manner during several of these particular stages. It can, for example, be used, completely or partially, during the manufacture of pulverulent mineral binders, including at the level of cement works, before, during and/or after crushing or during the preparation of dry and/or ready-to-use mortars or concretes. It can also be used, totally or partially, during transport of pasty or liquid mineral binders, or during their manufacture in the factory or on site, and for example in the mixing water and/or the necessary aggregates for preparation, notably in enclosures commonly called concrete batching and mixing plants.

As a result of which, the subject matter of the present invention is also respectively:

the use of such an additive for the preparation of a mineral binder, and the use of a composition containing at least one product of internal dehydration of a hydrogenated sugar, in particular of a dehydrated hexitol, for the preparation of such an additive or of a mineral binder.

The general concept of the present invention rests equally on the surprising and unexpected use of such a composition, on its own or within a more complex additive as:

an accelerating agent for setting and/or hardening of a mineral binder and/or an agent for improving the mechanical properties of a mineral binder in the hardened state.

And it is remarkable to note, as already emphasised, that such advantageous functionalities are expressed just as well at ordinary temperatures as at low temperatures.

The present invention will be described in an even more detailed manner with the aid of the following examples which are not restrictive in any way.

In all the examples which follow, the measurements of the spread (in mm) and of mechanical strength (in MPa) at 17 hours, 24 hours, 3 days or 28 days, have been made according to the standard CEN 196-01.

The measurement of the setting start times has been made according to the standard CEN 196-03.

EXAMPLE 1

A control mortar is prepared ("MORTAR T") according to the standard CEN 196-01, mixing 450 g HP LAFARGE 52.5 cement with 1350 g standardised sand and 225 g water.

The spread E is measured in mm, the start of setting DP in hours and minutes and the strength at 24 hours, 2 days and 28 days in MPa.

These strengths are measured after storing at 20° C. The mortar compositions are prepared in the same way, to which are added respectively:

MORTAR 1: 0.3% (in dry weight/dry weight of cement) of the above-mentioned PRODUCT B, i.e. of crystallised isosorbide with very high purity, MORTAR 2: 1% (dry/dry) of $CaCl_2$, MORTAR 3: 1% (dry/dry) $Li_2CO_3$, MORTAR 4: 1% (dry/dry) NaOH MORTAR 5: 1% (dry/dry) $H_2SO_4$, and MORTAR 6: 2% (dry/dry) of the product FRIOLITE® marketed by SIKA as an additive for concreting in cold weather.

The results obtained by MORTAR T without additive and mortars 1 to 6 are repeated below:

| MORTAR | E (mm) | DP (h:min) | R24H (MPa) | R2J (MPa) | R28J (Mpa) |
|---|---|---|---|---|---|
| MORTAR T | 232.5 | 5:0 | 10.1 | 24.4 | 48 |
| MORTAR 1 | 234.5 | 5:0 | 12.3 | 28 | 49 |
| MORTAR 2 | 242.5 | 2:50 | 17.3 | 34.4 | 54 |
| MORTAR 3 | 203.5 | 5:0 | 14.1 | 32.3 | 44.5 |
| MORTAR 4 | 228.5 | 4:15 | 15.8 | 30.1 | 40.5 |
| MORTAR 5 | 208 | 4:55 | 8.3 | 23.2 | 42.5 |
| MORTAR 6 | 206.5 | 4:30 | 12.9 | 25.3 | 44.5 |

These results show the advantages obtained, in MORTAR 1, by using an additive according to the invention constituted by a composition based on isosorbide, such as PRODUCT B This PRODUCT B does not have any negative influence on plasticity nor on the start of setting of the mortar.

In comparison with the results obtained with MORTAR T which has no additive, the introduction of PRODUCT B makes it possible to improve significantly (by 21.3%) the strength of the mineral binder when fresh.

It also improves the strength of the mineral binder at 2 days and 28 days.

The values at 28 days (R28J) are even greater than those obtained with standard accelerators of setting and/or of hardening such as $Li_2CO_3$ (MORTAR 3), NaOH (MORTAR 4), $H_2SO_4$ (MORTAR 5) or "FRIOLITE®" (MORTAR 6).

Moreover, certain of these usual products ($Li_2CO_3$, $H_2SO_4$ and "FRIOLITE®") have a negative effect on the plasticity of the mortar, the spread value E obtained (<210 mm) being considerably lower than 95% of the value measured for the control mortar (232.5 mm).

Within the framework of this EXAMPLE 1 it appears then that it is PRODUCT B which makes it possible to obtain the performances closest to those of a chlorinated additive constituted by $CaCl_2$. PRODUCT B can be considered here both as an agent for accelerating hardening and as an agent for improving the mechanical properties of the hardened mortar.

EXAMPLE 2

The strength of the above-quoted MORTARS 1 to 6, kept this time at a low temperature, i.e. at 5° C., is studied.

The results obtained are repeated below:

|  | R24H (MPa) | R2J (MPa) | R28J (MPa) |
| --- | --- | --- | --- |
| MORTAR 1 | 2.3 | 12.3 | 62 |
| MORTAR 2 | 6.9 | 15 | 62.5 |
| MORTAR 3 | 1.8 | 12 | 49 |
| MORTAR 4 | 3.7 | 14.5 | 51 |
| MORTAR 5 | 1.8 | 5.9 | 48 |
| MORTAR 6 | 2.1 | 12.5 | 48.5 |

The value at 24 hours obtained at 5° C. for MORTAR 1 (2.3 MPa) is greater than 20% of the value obtained at 20° C. for MORTAR T without an additive (10.1 MPa). This confirms the role played in accelerating hardening by the PRODUCT B contained in MORTAR 1.

Moreover, the results of this EXAMPLE 2 confirm the role played by this PRODUCT B in improving mechanical properties.

In a remarkable manner, the latter makes it possible, at 5° C., to achieve performances at 28 days practically identical to those of $CaCl_2$, and this despite an introduction rate which is three times lower.

EXAMPLE 3

From another batch of HP LAFARGE cement, the following compositions of mortar are prepared, as described in EXAMPLE 1, with or without an additive of 0.3% (dry/dry) of one or other of the following derivatives of sugar:

MORTAR T1: without additive (control)
MORTAR 7: PRODUCT B
MORTAR 8: sodium gluconate
MORTAR 9: glucose syrup GLUCIDEX® 29 *
MORTAR 10: dextrin TACKIDEX® DF 165 *
MORTAR 11: sorbitol syrup NEOSORB® 70/02 * *
   marketed by the Applicant Values of spread and of start of setting are obtained as below:

|  | E (mm) | DP (h:min) |
| --- | --- | --- |
| MORTAR T1 | 235.5 | 3:30 |
| MORTAR 7 | 236 | 2:50 |
| MORTAR 8 | 265 | >15:00 |
| MORTAR 9 | 247 | 12:45 |
| MORTAR 10 | 225 | 6:30 |
| MORTAR 11 | 229 | 7:00 |

Taken as a whole, these results show that an additive according to the invention such as PRODUCT B behaves differently from the other additives based on a derivative of sugar and particularly a sorbitol syrup. It makes it possible to accelerate the start of setting of the mortar and this whilst preserving a very acceptable plasticity. The measurement, at 20° C., of the strength at 17 hours has confirmed, moreover the role of PRODUCT B in accelerating hardening, the latter making it possible to reach a value of 10 MPa (MORTAR 7), significantly greater than that obtained for MORTAR T1 without any additive (8.5 MPa).

EXAMPLE 4

From a third batch of HP LAFARGE cement are prepared, as described in EXAMPLE 1, the following mortar compositions, with or without an additive of 0.3% (dry/dry) of one or other of the following additives according to the invention which have been described before:

MORTAR T2: without additive (control)
MORTAR 12: PRODUCT F
MORTAR 13: PRODUCT E
MORTAR 14: PRODUCT D
MORTAR 15: PRODUCT B For all these mortars are obtained the following values of spread and strength at 24 hours, 3 days and 28 days, these values being measured after storing at 20° C.

|  | E (mm) | R24H (MPa) | R3J (MPa) | R28J (MPa) |
| --- | --- | --- | --- | --- |
| MORTAR T2 | 222.5 | 13 | 30.8 | 45.5 |
| MORTAR 12 | 229 | 14.1 | 32.8 | 47 |
| MORTAR 13 | 228 | 14.2 | 31.9 | 46 |
| MORTAR 14 | 227.5 | 14.8 | 33.2 | 47.5 |
| MORTAR 15 | 225.5 | 15 | 35 | 47 |

Taken as a whole, these results confirm the interest of compositions based on product(s) of internal dehydration of a hydrogenated sugar such as sorbitol as additives for mineral binders, in particular as agents for accelerating hardening and as agents for improving the mechanical properties of the mineral binders in the hardened state.

They also show that products such as PRODUCTS D and F, less rich in isosorbide and sorbitan than PRODUCT B or D, can be used very validly in such applications.

EXAMPLE 5

The strength of the above-quoted MORTARS 12 to 15, this time at a low temperature, i.e. at 5° C., is studied.

The results obtained are repeated below:

|  | R24H (MPa) | R3J (MPa) | R28J (MPa) |
| --- | --- | --- | --- |
| MORTAR 12 | 3.6 | 17.4 | 58 |
| MORTAR 13 | 3.6 | 19.4 | 53 |
| MORTAR 14 | 3.7 | 20.0 | 52.5 |
| MORTAR 15 | 3.9 | 21.2 | 52 |

For all these mortars, the value obtained at 24 hours at 5° C. (3.6 to 3.9 MPa) represents considerably more than 20% (in this case between roughly 27.7 and 30%) of the value obtained at 24 hours, but at 20° C., with MORTAR T2 without any additive Similarly, the values obtained at 28 days at 5° C. (52 to 58 MPa) represent considerably more than 90% (in this case between roughly 114.3 and 127.5%) of the value obtained at 28 days, but at 20° C., with the MORTAR T2 without any additive.

This confirms the role of PRODUCTS B, D, E and F, usable as additives according to the invention, in accelerating hardening.

Supplementary tests have shown that the above-quoted PRODUCTS A and C, although less effective than PRODUCTS B, D, E, or F, were also capable, at a low temperature, of accelerating hardening and improving the characteristics of MORTAR T2.

EXAMPLE 6

From another batch of HP LAFARGE cement are prepared, as described in EXAMPLE 1, the following mortar compositions, with or without an additive of 0.4% (dry/dry) of one or other of the following additives according to the invention:

MORTAR T3: without additive (control)
MORTAR 16: PRODUCT B
MORTAR 17: PRODUCT G
MORTAR 18: PRODUCT H The values below for spread, start of setting and strength at 17 hours (at 20° C.) are obtained.

|  | E (mm) | DP (h:min) | R17H (MPa) |
| --- | --- | --- | --- |
| MORTAR T3 | 219.5 | 3:20 | 10.8 |
| MORTAR 16 | 225 | 3:00 | 12.6 |
| MORTAR 17 | 214.5 | 3:05 | 12.5 |
| MORTAR 18 | 222.5 | 2:55 | 12.9 |

These results confirm that such additives can be validly used as accelerators for setting and hardening.

They show, by comparison with the results obtained previously, that generally speaking the additives according to the invention can just as well be made up of mixtures of several products of internal dehydration of hydrogenated sugars as contain exclusively or in a large majority only one of these products (isosorbide, isomannide or sorbitan, for example).

Moreover, supplementary tests carried out on several batches of HTS LAFARGE 52.5 cement (low content of C3) have confirmed the good aptitude of these products to be used, at 20° C. or 5° C., as agents for accelerating setting and/or hardening or agents for improving mechanical properties of mineral binders.

EXAMPLE 7

From another batch of HP LAFARGE cement are prepared, as described in EXAMPLE 1, the following mortar compositions, with or without one or other of the additives below:

MORTAR T4: without additive (control),
MORTAR 19: 0.3% sorbitan trioleate SPAN 85, such as described in the above-mentioned patent JP 59 121143,
MORTAR 20: 1.0% sodium sulphate,
MORTAR 21: 1.0% lime,
MORTAR 22: 0.3% PRODUCT B,
MORTAR 23: 0.3% PRODUCT B+1.0% sodium sulphate,
MORTAR 24: 0.3% PRODUCT B+1.0% lime.

The values below for spread, start of setting and strength at 24 hours (at 5 and 20° C.) are obtained.

| MORTAR | E (mm) | DP (h:min) | R24H (5° C.) (MPa) | R24H (20° C.) (MPa) |
| --- | --- | --- | --- | --- |
| T4 | 231 | 3:20 | 2.7 | 14.0 |
| 19 | 238 | 4:45 | 1.7 | 12.3 |
| 20 | 227 | 3:35 | 3.3 | 17.4 |
| 21 | 230 | 3:20 | 3.3 | 16.5 |
| 22 | 237 | 3:40 | 3.1 | 15.9 |
| 23 | 237 | 4:00 | 3.7 | 18.6 |
| 24 | 233 | 3:35 | 4.3 | 17.5 |

These results confirm the interest of PRODUCT B which behaves differently from the additive of the sorbitan trioleate type. Indeed, the latter acts more like a product for retarding setting and hardening and this as much at 5° C. as at 20° C. Moreover, one notes that it can be advantageous to associate isosorbide (PRODUCT B) with standard accelerators such as lime or sodium sulphate.

Supplementary tests carried out on HTS LAFARGE 52.5 cements have confirmed overall all of these findings.

What is claimed is:

1. A process for accelerating setting and/or hardening of mineral binders, by admixing with the mineral binders a composition containing at least one product of internal dehydration of a hydrogenated sugar.

2. The process according to claim 1, wherein said dehydration product consists of dehydrated hexitol selected from the group consisting of isosorbide, isomannide, sorbitan, mannitan and any mixtures of at least any two of these products.

3. The process according to claim 1, wherein said composition has a content of dehydration product of at least 5%, the percentage being expressed in total dry weight of product of dehydration in relation to the dry weight of said composition.

4. The process according to claim 1, wherein said composition has a total content of isosorbide and sorbitan of at least 15%, the percentage being expressed in total dry weight of isosorbide and sorbitan in relation to the dry weight of said composition.

5. The process according to claim 1, wherein the hydrogenated sugar consists of hydrogenated monosaccharide selected from the group consisting of hexitols, pentitols, tetritols and their mixtures.

6. The process according to claim 3, wherein said composition has a content of dehydration product of at least 10%, the percentage being expressed in total dry weight of product of dehydration in relation to the dry weight of said composition.

7. The process according to claim 6, wherein said composition has a content of dehydration product of at least 40%, the percentage being expressed in total dry weight of product of dehydration in relation to the dry weight of said composition.

8. The process according to claim 4, wherein said composition has a total content of isosorbide and sorbitan of at least 55%, the percentage being expressed in total dry weight of isosorbide and sorbitan in relation to the dry weight of said composition.

9. The process according to claim 8, wherein said composition has a total content of isosorbide and sorbitan of at least 70%, the percentage being expressed in total dry weight of isosorbide and sorbitan in relation to the dry weight of said composition.

10. A process for improving the mechanical properties of mineral binders in the hardened state, by admixing with the mineral binders, a composition containing at least one product of internal dehydration of a hydrogenated sugar.

11. The process according to claim 10, wherein said dehydration product consists of dehydrated hexitol selected from the group consisting of isosorbide, isomannide, sorbitan, mannitan and any mixtures of at least any two of these products.

12. The process according to claim 10, wherein said composition has a content of dehydration product of at least 5%, the percentage being expressed in total dry weight of product of dehydration in relation to the dry weight of said composition.

13. The process according to claim 10, wherein said composition has a total content of isosorbide and sorbitan of at least 15%, the percentage being expressed in total dry weight of isosorbide and sorbitan in relation to the dry weight of said composition.

14. The process according to claim 10, wherein the hydrogenated sugar consists of hydrogenated monosaccharide selected from the group consisting of hexitols, pentitols, tetritols and their mixtures.

15. The process according to claim 12, wherein said composition has a content of dehydration product of at least 10%, the percentage being expressed in total dry weight of product of dehydration in relation to the dry weight of said composition.

16. The process according to claim 15, wherein said composition has a content of dehydration product of at least 40%, the percentage being expressed in total dry weight of product of dehydration in relation to the dry weight of said composition.

17. The process according to claim 13, wherein said composition has a total content of isosorbide and sorbitan of at least 55%, the percentage being expressed in total dry weight of isosorbide and sorbitan in relation to the dry weight of said composition.

18. The process according to claim 17, wherein said composition has a total content of isosorbide and sorbitan of at least 70%, the percentage being expressed in total dry weight of isosorbide and sorbitan in relation to the dry weight of said composition.

* * * * *